United States Patent [19]

Hillenbrand et al.

[11] 4,138,560

[45] Feb. 6, 1979

[54] PROCESS FOR COOLING MELAMINE SYNTHESIS WASTE GASES

[75] Inventors: Engelbert Hillenbrand, Heppenheim; Hermann D. Fromm, Gruenstadt; Alfred Widmann, Mutterstadt, all of Fed. Rep. of Germany

[73] Assignee: BASF Aktiengesellschaft, Ludwigshafen, Fed. Rep. of Germany

[21] Appl. No.: 864,323

[22] Filed: Dec. 27, 1977

Related U.S. Application Data

[63] Continuation of Ser. No. 688,762, May 21, 1976, abandoned.

[30] Foreign Application Priority Data

Jun. 10, 1975 [DE] Fed. Rep. of Germany ....... 2525781

[51] Int. Cl.$^2$ .................. C07D 251/60; C07D 251/62
[52] U.S. Cl. ....................................... 544/203; 55/84; 544/201
[58] Field of Search ................................ 544/201, 203

[56] References Cited

U.S. PATENT DOCUMENTS

| | | | |
|---|---|---|---|
| 3,310,558 | 3/1967 | Oele et al. | 544/203 |
| 3,386,999 | 6/1968 | Manes | 544/201 |
| 3,513,167 | 5/1970 | Fromm et al. | 544/203 |
| 3,682,911 | 8/1972 | Kaasenbrood et al. | 544/201 |
| 3,697,519 | 10/1972 | Kaasenbrood | 544/203 |
| 3,700,672 | 10/1972 | Kokubo et al. | 544/201 |
| 3,708,536 | 1/1973 | Hillenbrand | 544/201 |
| 3,979,392 | 9/1976 | Eguchi et al. | 544/203 |

*Primary Examiner*—John M. Ford
*Attorney, Agent, or Firm*—Keil, Thompson & Shurtleff

[57] ABSTRACT

Melamine synthesis waste gases are first treated for the removal of melamine by condensation. The waste gases are then treated with urea-containing melts which are cooled indirectly. At least parts of said indirect cooling takes place together with the treatment of the reaction waste gases with the urea-containing melts in a single zone.

7 Claims, No Drawings

PROCESS FOR COOLING MELAMINE SYNTHESIS WASTE GASES

This is a continuation of application Ser. No. 688,762 filed May 21, 1976, now abandoned.

This invention relates to a process for cooling melamine synthesis waste gases by treating them, after the separation of the melamine, with urea-containing melts, by indirect cooling, at a temperature just above their melting point.

It is well known to manufacture melamine by heating urea or its thermal decomposition products to temperatures of from 350° to 450° C. at atmospheric or elevated pressures of up to about 10 atmospheres in the presence of catalysts and added ammonia or gas mixtures containing ammonia, such as ammonia/carbon dioxide mixtures, e.g. the reaction waste gases of the melamine synthesis itself The vaporous melamine is separated from the reaction gases by fractional condensation by cooling said gases to temperatures of from 150° to 250° C. These gases thus freed from melamine contain unreacted urea which, as is also well known, may be washed out by direct contact of these gases with melts of urea or with a melt of a mixture of urea and biuret and also possibly containing other decomposition products of urea such as cyanuric acid, in which case the gases are subjected to further cooling. The urea required for this treatment is advantageousy recycled and is brought into direct contact with the reaction gases. The reaction gas thus cooled is then separated from the urea melt together with the components absorbed therein from the gas or the thermal decomposition products of urea (melamine, urea, cyanuric acid, biuret, etc.) formed therein. The reaction gases thus purified and cooled are used partly as fluidizing gas for the catalyst in the synthesis reactor and/or as cooling gas for separation of the melamine.

The fact that the urea required in the synthesis reactor is removed from this circulation means that the components contained therein as a result of washing the reaction gas or as a result of thermal decomposition are recycled to the melamine synthesis and thus increase the yield. Furthermore, the amount of byproducts in the urea circulation is held at a constant, low level.

The heat absorbed by the circulated urea during cooling and purification of the reaction gases may be used, for example, for melting the fresh urea required for the synthesis and the remainder or, alternatively, all of the heat may be removed in a cooler by indirect cooling.

It has been found that deposits on the cooling surfaces of the urea cooler cannot be avoided and make it necessary to clean the cooler at intervals. Moreover, temperature control in the urea cooler is problematic, since the temperature of the heat exchanger surfaces must nowhere fall below the solidification point of the urea melt. The difficulty encountered here is the fact that the solidification point of the urea melt changes constantly, since the content of byproducts such as biuret and the like in the melt fluctuates and these fluctuations strongly affect the solidification point.

It is an object of the present invention to provide a process for cooling the melamine synthesis waste gases produced by catalytic conversion of urea at elevated temperatures and separation of the thus formed melamine from the resulting synthesis gas by condensation wherein the synthesis waste gases are treated, after the separation of the melamine, with urea-containing melts maintained, by indirect cooling, at a temperature just above their melting point, in which process the aforementioned drawbacks do not occur.

We have now found that this object may be achieved by carrying out at least part of the cooling of the melts in a single zone together with the treatement of the reaction waste gases, the cooling medium having a temperature which is at least 3° C. below the temperature of the melt. Thus in the process of the invention, cooling of the melts used for treating the reaction offgases and consisting of or containing urea is carried out at least partially directly within the treatment chamber for the reaction offgases as opposed to outside the treatment chamber in the prior art process. The said treatment is carried out in conventional manner in washing columns, of which the walls are also available for the removal of heat, for example by irrigation.

According to a preferred embodiment of the process of the invention, gas and melt pass to the top of the column where they are passed cocurrently over cooling surfaces and together give off their heat to said cooling surfaces. The urea melt is heated only slightly, if at all, which means, unlike the prior art processes, that the formation of insoluble thermal decomposition products in the urea is greatly suppressed. Since the method of the invention thus enables lower temperatures of melt and gas to be achieved, there is the added advantage that in the aforementioned fractional condensation of melamine either smaller apparatus volumes can be used or a greater separating capacity can be achieved.

The reaction offgases fed to the treatment chamber usually have a temperature of from 150° to 250° C., preferably from 190° to 220° C.

The melts used for treating the reaction offgases may be not only pure urea melts having a solidification point of 132.7° C. but also melts containing, in addition to urea, its thermal decomposition products such as biuret and/or cyanuric acid, which has the advantage that the melting point of the urea is lowered. For example, urea melts having a biuret content of 20% have a melting point of 120° C. and those having a biuret content of about 40%, corresponding to the eutectic mixture, have a melting point of above 110° C. For example, melts are used having a melting point between about 110° and 132.7° C. and accordingly containing biuret in an amount above that contained in the eutectic mixture. As mentioned above, the urea-containing melts may also contain other decomposition products of urea, such as cyanuric acid, or even melamine itself or other compounds which do not react with the melt or components of the reaction offgas, for example ammonium carbamate, ammonium rhodanide and ammonium nitrate. At all events the solidification point of the melts should be within the range given above.

The molten urea or urea-containing melts are fed to the washing columns at temperatures just above the solidification point of the melt in question, i.e. usually at a temperature which is about 10° C. and preferably about 5° C. higher than said solidification point.

During the treatment of the reaction waste gases by the process of the invention, heat may be removed from the gases and the melt at such a rate that the temperature of the melt does not fall below its solidification point whilst on the other hand the temperature of the melt is not raised to any substantial extent. On account of the intimate contact between the melts and reaction gas, the latter is cooled to the temperature of the melt which simultaneously absorbs the unreacted urea contained in the gases and any melamine still present. It is possible, however, to allow the temperature of the melt to rise above its inlet temperature, in which case the temperature of the melt is lowered outside the treatment chamber. This procedure is advantageous when it is desired to utilize the heat absorbed by the melt and not given off in the treatment zone for other purposes, for example for melting fresh urea to be used for the synthesis. Preferably, the temperature of the melt on leaving the zone should not be more than 4° C. above its temperature on entering the zone. The advantages of the process of the invention are fully realized in such cases.

It has been found, surprisingly, that the internal coolers arranged in the washing columns remain free from deposits even when operated over a period of months, although the cooling medium must, in order to have a cooling effect, exhibit a temperature which is at least 3° C. below the solidification point of the melt to be cooled. But even in the case of much greater temperature differences such as occur when use is made of river water, whose temperature may be from about 0° to 30° C. depending on the time of year, there are surprisingly no deposits of urea decomposition products or solidified melt. On account of this fact, it is preferred to use cooling media whose temperatures are at least 50° C. below the solidification point of the melt. The lower limit of the temperature of the cooling medium is usually about 0° C.

The possibility of being able to maintain much greater temperature differences between the cooling medium and the temperature of the melt in the process of the invention gives the further advantage of using much smaller cooling areas.

To avoid the occurrence of stress-crack corrosion, it is advantageous to use a cooling medium which is free from chlorine or chloride, preferably condensed water, in place of river water. The heat absorbed by the cooling medium in the washing column can then be removed by river water.

EXAMPLE (A) 100,00 m$^3$ of a reaction offgas are passed, per hour, to the top of a co-current washer at a temperature of 225° C., where they are washed with 600 m$^3$/hr of a circulated urea/biuret melt having a temperature of 130° C. The temperature of the melt rises during said treatment to 136° C. Heat is removed from the melt in an evaporative cooler disposed outside the washer. To prevent the urea from crystallizing out at short intervals, the temperature of the water must not be below 120° C.

The gas withdrawn from the column has a temperature of 138° C.

The cooling efficiency is calculated from the values found for the average logarithmic temperature difference t = 13° C. and the average rate of heat transfer k = 500 kcal/m$^2$/hr/° C. to give a value of about 6,500 kcal/m$^2$.

The coolers must be cleaned once a month.

(B) The gas is cooled as described in (A) above, except that the heat is removed by an internal cooler disposed within the cocurrent washer. The coolant in the cooler consists of 200 m$^3$/hr of condensed water which is warmed from 20° C. to 31.5° C. during the cooling operation. The melt is withdrawn from the washer at a temperature of 130° C. and the gas at a temperature of 132° C.

The cooling efficiency calculated from the values found is about 29,000 kcal/m$^2$.

The cooler remains free from deposits even after continuous operation over a period of months.

(C) the gas is cooled as described under (A) above, except that part of the heat absorbed by the melt is removed by a cooler disposed within the cocurrent washer. The coolant in this cooler consists of 67 m$^3$/hr of condensed water which is warmed from 20° C. to 31.5° C., during the cooling. The melt leaves the washer at a temperature of 134° C., the gas at a temperature of 136° C.

The melt is recooled to 130° C. in a cooler disposed outside the co-current washer.

The internal cooler remains free from deposits even when operated continuously over a period of months.

We claim:

1. In a process for the synthesis of melamine by the catalytic conversion of urea at elevated temperatures in the presence of ammonia, thereby producing a synthesis gas containing unreacted urea and melamine vapors, and cooling said synthesis gas to 150°-250° C. to separate therefrom most of the melamine by fractional condensation of the melamine from the resulting waste gases, which waste gases contain a small amount of melamine and also unreacted urea, the improvement which comprises passing said waste gases at an initial temperature 150°-250° C. and a melt of urea, optionally containing at least one of biuret, cyanuric acid and melamine through a cooling zone, said melt having an initial temperature just above its melting point which is within the temperature range of 110° C. to 132.7° C., with direct contact between said waste gases and said melt, the temperature of said waste gases thereby being lowered in said zone to substantially the temperature of said melt, said cooling zone containing indirect heat exchange cooling surfaces contacted by said melt and said waste gases as they pass through said cooling zone, employing a cooling medium to cool said indirect heat exchange surfaces, said cooling medium having a temperature which is at least 3° C. below the solidification point of said melt, and removing heat from said cooling zone by said cooling surfaces at such a rate that the temperature of said melt in said cooling zone does not fall below its solidification point while avoiding substantial increases in temperature of said melt in said cooling zone, and withdrawing from said cooling zone the melt which has passed therethrough and in which the urea and the melamine in said waste gases has been absorbed.

2. A process as claimed in claim 1, wherein said initial temperature of said waste gases is in the range of 190° to 220° C.

3. A process as claimed in claim 1, wherein said melt is one containing urea and at least one of biuret and cyanuric acid.

4. A process as claimed in claim 1, wherein the melt which is fed to said cooling zone has a temperature up to 10° C. above its melting point.

5. A process as claimed in claim 1, wherein the temperature of the melt withdrawn from said cooling zone has a temperature which is not more than 4° higher than the temperature of the melt which is fed to said cooling zone.

6. A process as claimed in claim 1, wherein said cooling medium has a temperature which is at least 50° C. below the solidification point of said melt.

7. A process as claimed in claim 1, wherein the melt which is fed to said cooling zone consists essentially of urea.

* * * * *